United States Patent [19]

Eppinger et al.

[11] Patent Number: 5,228,907
[45] Date of Patent: Jul. 20, 1993

[54] POLYMERIZABLE DENTAL MATERIAL

[75] Inventors: Regina Eppinger; Bernhard Eppinger, both of Weilburg; Detlef Heindl, Weinbach; Peter J. Kohler, Bad Nauheim; Joachim Fritze, Friedrichsdorf, all of Fed. Rep. of Germany

[73] Assignee: Heraeus Kulzer GmbH, Hanau, Fed. Rep. of Germany

[21] Appl. No.: 788,985

[22] Filed: Nov. 7, 1991

[30] Foreign Application Priority Data

Nov. 17, 1990 [DE] Fed. Rep. of Germany ....... 4036675
Apr. 2, 1991 [DE] Fed. Rep. of Germany ....... 4110612

[51] Int. Cl.$^5$ ............................................... C09K 3/00
[52] U.S. Cl. ...................................... 106/35; 523/115; 523/116
[58] Field of Search .................... 106/35; 523/115, 116

[56] References Cited

U.S. PATENT DOCUMENTS

| | | | |
|---|---|---|---|
| 3,066,112 | 11/1962 | Bowen | 523/116 |
| 3,539,533 | 11/1970 | Lee et al. | 526/211 |
| 4,029,632 | 6/1977 | Grosse et al. | 524/526 |
| 4,071,424 | 1/1978 | Dart et al. | 204/159 |
| 4,267,097 | 5/1981 | Michl et al. | 524/526 |
| 4,281,991 | 8/1981 | Michl et al. | 433/202 |
| 4,351,853 | 9/1982 | Jochum et al. | |
| 4,388,069 | 6/1983 | Orlowski | 433/228 |
| 4,407,984 | 10/1983 | Ratcliffe et al. | 523/115 |
| 4,427,799 | 1/1984 | Orlowski et al. | 523/116 |
| 4,459,193 | 7/1984 | Ratcliffe et al. | 204/159.23 |
| 4,522,694 | 6/1985 | Schaefer | 204/159.24 |
| 4,649,165 | 3/1987 | Kuhlmann | 523/116 |
| 4,746,685 | 5/1988 | Masuhara et al. | 522/13 |
| 4,824,876 | 4/1989 | Matsumoto et al. | 522/24 |
| 4,923,905 | 5/1990 | Masuhara et al. | 522/24 |
| 5,009,597 | 4/1991 | Schaefer et al. | |
| 5,028,638 | 7/1991 | Held et al. | 522/14 |

FOREIGN PATENT DOCUMENTS

| | | |
|---|---|---|
| 0064834 | 11/1982 | European Pat. Off. . |
| 0053442 | 5/1983 | European Pat. Off. . |
| 0091990 | 10/1983 | European Pat. Off. . |
| 0116121 | 8/1984 | European Pat. Off. . |
| 0156105 | 10/1985 | European Pat. Off. . |
| 0176777 | 4/1986 | European Pat. Off. . |
| 0382033 | 4/1991 | European Pat. Off. . |
| 2403211 | 7/1975 | Fed. Rep. of Germany . |
| 2405578 | 8/1975 | Fed. Rep. of Germany . |
| 3001616 | 7/1981 | Fed. Rep. of Germany . |
| 3441564 | 5/1986 | Fed. Rep. of Germany . |
| 3403040 | 3/1988 | Fed. Rep. of Germany . |
| 3708618 | 9/1988 | Fed. Rep. of Germany . |
| 3826233 | 10/1989 | Fed. Rep. of Germany . |
| 4002726 | 9/1990 | Fed. Rep. of Germany . |
| 1408265 | 10/1975 | United Kingdom . |
| 81/02254 | 8/1981 | World Int. Prop. O. . |

OTHER PUBLICATIONS

Schweiz. Monatsschr. Zahnmed, vol. 99, Apr. 1989 (Swiss Monthly on Dentistry).
Die Quintessenz, 1988, pp. 1243-1253.

Primary Examiner—Mark L. Bell
Assistant Examiner—Margaret Einsmann
Attorney, Agent, or Firm—Frishauf, Holtz, Goodman & Woodward

[57] ABSTRACT

Radiopaque, abrasion-resistant tooth fillings and inlays that can be polished to a high gloss can be made from a dental material that, in addition to monomeric dimethacrylates, contains a filler mixture of 80 to 90 weight % barium aluminum silicate glass, having a mean particle size of 0.5 to 1.5 μm, and 10 to 20 % weight silicon dioxide, having a mean particle size of 0.04 to 0.06 μm. The dental material is also suitable for anchoring dental prostheses.

19 Claims, No Drawings

POLYMERIZABLE DENTAL MATERIAL

CROSS-REFERENCE TO RELATED APPLICATION

U.S. Ser. No. 07/596,099, filed Oct. 9, 1990 now U.S. Pat. No. 5,089,051 issued Feb. 18, 1992.

BACKGROUND OF THE INVENTION

1. Field of the Invention

The invention relates to a polymerizable dental material containing monomeric dimethacrylates, an inorganic filler mixture of barium aluminum silicate glass and microfine silicon dioxide and an α-diketone/amine system for the photopolymerization.

The dental material according to the invention furnishes a tooth filling material, a material for producing inlays, and a dental anchoring cement.

2. Background Information

Polymerizable tooth filling materials have been known for many years. The earliest of these materials comprised mixtures of monomeric and polymeric methyl methacrylate which harden within a few minutes, at the temperature conditions prevailing in the mouth, by addition of a catalyst or a system comprising a catalyst and an accelerator.

Improvement in the mechanical properties of these filling materials was achieved by adding fine-grained fillers, such as quartz or aluminum silicates; improvement in the esthetic effect was achieved by developing new catalyst systems that no longer cause discoloration; and a reduction in polymerization shrinkage was achieved by using methacrylates of higher alcohols in addition to, or instead of, methyl methacrylate.

The first of these new materials was developed by Rafael L. Bowen and is described in U.S. Pat. No. 3,066,112. As a monomer binder, it substantially contains a diacrylate or dimethacrylate prepared by the reaction of bisphenol with glycidyl acrylate or methacrylate, and as an inorganic filler it contains fine-grained silicon dioxide, preferably in silanized form. Bis-[4-(2-hydroxy- 3-methacryloyloxypropoxy)phenyl]dimethylmethane invented by Bowen, also known as "bis-GMA" or "Bowen monomer", is still today included in most of the dental compositions available on the market.

An example of a further composite—a dental material that in addition to organic monomers contains a fine-grained inorganic filler—is described in U.S. Pat. No. 3,539,533. The polymerizable binder is a mixture of bis-GMA; bisphenol A dimethacrylate; a diluting monomer, in particular triethylene glycol dimethacrylate; and optionally a small quantity of methacrylate, which is used together with approximately 65 to 75 weight % of the inorganic filler, for example, silicon dioxide, glass, aluminum oxide or quartz. The inorganic filler may have a particle size of approximately 2 to 85 $\mu$m; it is pretreated with a silane, such as 3-methacryloyloxypropyltrimethoxysilane, to improve the plastic/filler bond.

From German Patent 24 03 211, a material for dental purposes (filling materials for cavities, materials for anchoring cements, sealing and protective coating compositions, crown and bridge materials, prosthesis materials, and compositions for making false teeth) is known, which in addition to polymerizable acrylate or methacrylate contains microfine (microdispersed) silicon dioxide having a particle size of approximately 10 to 400 millimicrometers as an inorganic filler. The polymerizable monomer comprises bis-GMA or some other derivative of bisphenol A or a reaction product of hydroxyalkyl methacrylates and diisocyanates, optionally together with monomeric short-chained methacrylates and/or diacrylates or dimethacrylates. The tooth fillings and the like made from the material containing the microfine filler are distinguished by their capacity to be polished to a high gloss.

From German Patent 24 05 578, in a dental material to be processed into products that can be polished to a high gloss, it is known to use not only esters of methacrylic acid as an inorganic filler, but also a mixture of silicic acid with a maximum particle size of 0.07 $\mu$m and fine-grained glass, the particle size of which should not exceed 5 $\mu$m. Bis-GMA, 2,2-bis-[p-(2- hydroxyethoxy)-phenyl]propane dimethacrylate and triethylene glycol dimethacrylate are named in German Patent 24 05 578 as methacrylates.

A dental material containing both conventional and microfine inorganic fillers—which has come to be known as a hybrid composite—is described, for example, in International Patent Application WO 81/02 254, as well. It contains a filler mixture of hydrophobic silicon dioxide having a diameter of 0.01 to 0.04 $\mu$m and glass, for instance radiopaque glass containing barium or strontium, having a diameter of 2 to 30 $\mu$m. As the polymerizable monomers, bis-GMA or ethoxylated bisphenol A dimethacrylate and triethylene glycol dimethacrylate are used. The material is used as a tooth filling material and for hiding cast gold crowns, for example.

German Patents 37 08 618 and 38 26 233 relate to plastic tooth replacement parts having an abrasion-resistant jacket, which can be polished to a high gloss, of 10 to 90 weight % plastic containing microdispersed silicon dioxide having a particle size of 0.01 to 0.4 $\mu$m. The jacket surrounds a core which has a high bending strength and a high bending modulus, and which contains 30 to 90 weight % of an inorganic filler mixture of 60 to 100 weight % of silicon dioxide, lithium aluminum silicate glass and/or strontium aluminum silicate glass having a mean particle size of 0.7 to 5 $\mu$m or barium aluminum silicate glass having a mean particle size of 0.7 to 10 $\mu$m, and 0 to 40 weight % of microdispersed silicon dioxide having a mean particle size of 0.01 to 0.4 $\mu$m. The plastic of the core and jacket is preferably a polymer comprising bis-GMA, ethoxylated bisphenol A diacrylate or dimethacrylate, triethylene glycol dimethacrylate, dodecanediol dimethacrylate, diurethane dimethacrylate made from 2-hydroxyethyl methacrylate and 2,2,4-trimethylhexamethylene diisocyanate, bis-(acryloyloxymethyl)tricyclo-[5.2.1.0$^{2,6}$]decane, and/or bis- (methacryloyloxymethyl)tricyclo-[5.2.1.0$^{2,6}$]decane. The dental prosthetic parts are suitable for supplying crowns, bridges, inlays, and the like.

Dental anchoring cements are used to bond inlays, onlays, crowns, bridges, and so-called adhesive bridges (Maryland bridges), veneer shells and the like to the tooth substance. Besides cements that harden as a consequence of curing processes, such as the zinc oxide phosphate cements, those that cure by polymerization are also increasingly used. The polymerizable anchoring cements typically contain esters of acrylic acid or methacrylic acid, as monomers, and usually contain a fine-grained inorganic filler, along with the catalysts that trigger the polymerization.

European Patent Disclosure Document B1 0 064 834 discloses an adhesive, for bonding an object to a tooth, that contains a binder resin, a diluting monomer, an inorganic filler in a quantity of at least 20% by weight, and a photoinitiator for triggering the polymerization upon irradiation with visible light. As the photoinitiator, a mixture of an α-diketone, selected, for example, from camphor quinone, benzil, biacetyl, 9,10-phenanthrene-quinone and naphthoquinone, and an amine, particularly a dialkanolamine or trialkanolamine, is used. As fillers, inorganic glasses, such as barium aluminum silicate glass and lithium aluminum silicate glass, are preferred.

According to German Patent 34 41 564, the metal surfaces of adhesive bridges can be bonded to the dental enamel firmly, tightly and without gaps if the adhesive used for this purpose contains not only methacrylates and inorganic filler comprising silanized silicon dioxide having a particle size of up to 0.04 μm, but also both a catalyst for chemical cold polymerization (autopolymerization) and a catalysts for photopolymerization.

A low-viscosity micro-filled composite cement is known from Schweiz Monatsschr. Zahnmed. [Swiss Monthly for Dentistry], Vol. 99, 4/1989, which is hardened by two-stage photopolymerization and is initially colored yellow and receives its definitive color only through the final hardening. This cement contains two initiator systems having a high proportion of camphorquinone (camphoroquinone) for the photopolymerization, the absorption maxima of which is at various wavelengths of visible light. Initial hardening takes place with light at a wavelength greater than 470 nm, and final hardening takes place with light having a wavelength of around 470 nm.

Because the color of the cement initially differs from the tooth color, and because of its marzipan-like consistency after initial hardening, the cement is easily worked, and any excess of cement can be removed quickly and safety without damaging the tooth substance. This cement is not suitable for restorations that have regions inaccessible to light.

SUMMARY OF THE INVENTION

An object of the invention is to provide a photopolymerizable dental material, of the type described above, from which products can be made by polymerization that have the characteristics of radiopacity, abrasion resistance, the capability of being polished to a high gloss, and high mechanical strength values, especially high bending strength and bending modulus values. The dental material are usable as filling material for the front and side regions of the mouth, to make inlays, and as a anchoring cement.

The dental material of the present invention comprises 10 to 60 weight % bis-[4-(2-hydroxy-3-methacryloyloxypropoxy)phenyl]dimethylmethane, triethylene glycol dimethacrylate and/or diurethane dimethacrylate made from 2,2,4-trimethylhexamethylene diisocyanate and 2-hydroxyethyl methacrylate, 37 to 87 weight % of a filler mixture of 80 to 90 weight % barium aluminum silicate glass having a mean particle size of 0.5 to 1.5 μm and 10 to 20 weight % of microfine silicon dioxide having a mean particle size of 0.04 to 0.06 μm, and a photoinitiator system comprising 0.02 to 2 weight % α-diketone and 0.1 to 1 weight % amine.

DETAILED DESCRIPTION OF THE INVENTION

The inorganic filler mixture of the dental material of the present invention is preferably used in silanized form, for instance by treatment with 3- methacryloyloxypropyltrimethoxysilane.

Suitable α-diketone/amine systems, which trigger the polymerization of the monomers upon being irradiated with visible light at a wavelength of 320 to 500 nm, are known for instance from British Patent B1 1,408,265. Camphorquinone (Camphoroquinone) has proved to be especially suitable as an α-diketone. If the material is to be available as an anchoring cement that is initially non-tooth colored, but after irradiation with visible light is tooth-colored, then as the α-diketone a mixture of 0.01 to 1 weight % camphorquinone (camphoroquinone) and 0.01 to 1 weight % of 9,10-phenanthrenequinone is used. Preferably, it contains 0.02 to 0.05 weight % camphorquinone (camphoroquinone), 0.02 to 0.05 weight % 9,10-phenanthrenequinone, and 0.3 to 0.5 weight % amine.

As amines, N,N-bis-(2-hydroxyethyl)-p-toluidine and esters of 4-dimethylaminobenzoic acid, such as ethyl and butoxyethyl ester, have proved especially suitable.

It has proved additionally favorable to add to the dental material, as a further photoactive ingredient, a benzoyl compound, for example a benzil acetal, preferably in a quantity of from 0.02 to 0.1 weight %.

Coloring pigments, antioxidants, UV stabilizers and other typical additives can also be added to the dental material.

As an anchoring cement, the dental material has proved especially suitable if it contains not only the photoinitiator system, but also the catalyst for the autopolymerization. With such a cement, because its curing takes place both chemically and photochemically, a dental prosthesis can be firmly bonded to the tooth substance even in regions inaccessible to light, where no photopolymerization is possible.

For the sake of additional autopolymerization, the dental material preferably contains an organic peroxide, such as diacetylperoxide, dibenzoylperoxide or di-tert.-butylperoxide, which together with the amine forms a redox system. Redox systems of this type are known catalysts for the autopolymerization of acrylate- or methacrylate-based dental materials.

The dental material according to the invention is distinguished by good adhesion to the dental tissue and good workability and modelability, while the products made from it are distinguished by radiopacity, abrasion resistance, the capacity to be polished to a high gloss, and good mechanical properties—a high bending strength (120 MPa) and a high bending modulus (8000 to 120,000 MPa) are especially characteristic of the material.

For use, it has proved practical to furnish the dental material, if it contains methacrylate, an inorganic filler, a photoinitiator system, and optionally desired additives, in paste form, as a single-ingredient, storable material.

If the dental material is also to be used as an anchoring cement to be hardened by autopolymerization, then it is preferably in the form of a two-ingredient paste material; suitably, the composition of one paste is equivalent to that of the single-ingredient material, and the other paste includes, in addition to methacrylate and an inorganic filler, a catalyst for self-polymerization, that is, e.g. a peroxide.

The anchoring cement according to the invention is suitable for anchoring any type of dental prosthesis, made of ceramic, glass ceramic or composite material, as well as adhesive bridges to the tooth substance.

For example, if a tooth cavity is to be filled with an inlay made of a composite material, with the aid of an anchoring cement containing camphorquinone (camphoroquinone) and 9,10-phenanthrenequinone, then first the anchoring cement is applied to the walls of the cavity and to the inlay, as far as it extends into the cavity. Then the inlay is pressed into the cavity. Any excess anchoring cement, which can be readily distinguished by its yellow color from the tooth substance and which has a soft consistency, is removed with a suitable instrument, without damaging the tooth substance, and anchoring cement present in the gap between the cavity and the inlay is removed. Next, the anchoring cement is irradiated, with a light unit of the kind, for example, known for curing photopolymerizable tooth filling material, long enough that the yellow color disappears and the anchoring cement is thus completely cured.

For the purpose of further explanation, embodiments of the dental material according to the invention are described in the following non-limiting examples.

Example 1
Tooth filling and inlay material to be cured by photopolymerization

| | weight % |
|---|---|
| bis-GMA | 14 |
| triethylene glycol dimethacrylate | 7 |
| barium aluminum silicate glass silanized with 3-methacryloyloxypropyltrimethoxysilane, mean particle size 0.7 μm | 69.7 |
| silicon dioxide silanized with 3-methacryloyloxypropyltrimethoxysilane, mean particle size 0.04 to 0.06 μm | 8 |
| camphorquinone (camphoroquinone) | 0.4 |
| benzildimethylacetal (1,2-diphenyl-2,2-dimethoxyethanone) 10% solution in triethylene glycol dimethacrylate | 0.6 |
| 4-dimethylaminobenzoic acid butoxyethyl ester | 0.3 |

Example 2
Anchoring cement, in the form of a paste, to be cured by photopolymerization

| | weight % |
|---|---|
| bis-GMA | 30.00 |
| triethylene glycol dimethacrylate | 16.58 |
| barium aluminum silicate glass silanized with 3-methacryloyloxypropyltrimethoxysilane, particle size 0.7 μm | 40.80 |
| silicon dioxide silanized with 3-methacryloyloxypropyltrimethoxysilane, mean particle size 0.04 to 0.06 μm | 10.20 |
| camphorquinone (camphoroquinone) 10% solution in triethylene glycol dimethacrylate | 1.02 |
| benzildimethylacetal (1,2-diphenyl-2,2-dimethoxyethanone), 10% solution in triethylene glycol dimethacrylate | 0.60 |
| N,N-bis-(2-hydroxyethyl)-p-toluidine | 0.40 |
| 2-hydroxy-4-n-octyloxybenzophenone (UV stabilizer) | 0.40 |

Example 3
Anchoring cement, in the form of a paste, to be cured by photopolymerization

| | weight % |
|---|---|
| bis-GMA | 13.51 |
| triethylene glycol dimethacrylate | 7.28 |
| barium aluminum silicate glass silanized with 3-methacryloyloxypropyltrimethoxysilane, mean particle size 0.7 μm | 66.00 |
| silicon dioxide silanized with 3-methacryloyloxypropyltrimethoxysilane, mean particle size 0.04 to 0.06 μm | 10.79 |
| camphorquinone (camphoroquinone) 10% solution in triethylene glycol dimethacrylate | 1.00 |
| 9,10-phenanthrenequinone | 0.02 |
| benzildimethylacetal (1,2-diphenyl-2,2-dimethoxyethanone), 10% solution in triethylene glycol dimethacrylate | 0.60 |
| N,N-bis-(2-hydroxyethyl)-p-toluidine | 0.40 |
| 2-hydroxy-4-n-octyloxybenzophenone (UV stabilizer) | 0.40 |

Example 4
Anchoring cement, in the form of two pastes, to be cured by photopolymerization and autopolymerization

| Paste A | weight % |
|---|---|
| bis-GMA | 13.51 |
| triethylene glycol dimethacrylate | 7.28 |
| barium aluminum silicate glass silanized with 3-methacryloyloxypropyltrimethoxysilane, mean particle size 0.7 μm | 66.00 |
| silicon dioxide silanized with 3-methacryloyloxypropyltrimethoxysilane, mean particle size 0.04 to 0.06 μm | 10.79 |
| camphorquinone (camphoroquinone) 10% solution in triethylene glycol dimethacrylate | 1.00 |
| 9,10-phenanthrenequinone | 0.02 |
| benzildimethylacetal (1,2-diphenyl-2,2-dimethoxyethanone), 10% solution in triethylene glycol dimethacrylate | 0.60 |
| N,N-bis-(2-hydroxyethyl)-p-toluidine | 0.40 |
| 2-hydroxy-4-n-octyloxybenzophenone (UV stabilizer) | 0.40 |

| Paste B | weight % |
|---|---|
| diurethane dimethacrylate of 1 Mol 2,2,4-trimethylhexamethylene diisocyanate and 2 Mol 2-hydroxyethyl methacrylate | 15.33 |
| triethylene glycol dimethacrylate | 6.58 |
| barium aluminum silicate glass silanized with 3-methacryloyloxypropyltrimethoxysilane, mean particle size 0.7 μm | 8.12 |
| silicon dioxide silanized with 3-methacryloyloxypropyltrimethoxysilane, mean particle size 0.04 to 0.06 μm | 9.53 |
| dibenzoylperoxide | 0.44 |

Before use, pastes A and B are mixed together in a ratio of 1:1.

What is claimed is:

1. A polymerizable dental material, comprising:
   (a) 10 to 60 weight % of a monomeric dimethacrylate component comprising at least one of bis-(4-(2-hydroxy-3-methacryloyloxypropoxy)phenyl)dimethylmethane, triethylene glycol dimethacrylate and diurethane dimethacrylate made from 2,2,4-trimethylhexamethylene diisocyanate and 2-hydroxyethyl methacrylate,
   (b) 37 to 87 weight % of an inorganic filler mixture comprising 80 to 90 weight % barium aluminum silicate glass having a mean particle size of about 0.7 μm and 10 to 20 weight % of microfine silicon dioxide having a mean particle size of 0.04 to 0.06 μm,
   (c) 0.02 to 2 weight % of a α-diketone,
   (d) 0.1 to 1 weight % amine and
   (e) 0.02 to 0.1 weight % benzildimethylacetal.

2. The dental material of claim 1, wherein the inorganic filler mixture is silanized.

3. The dental material of claim 2, wherein the inorganic filler mixture is silanized with 3-methacryloyloxypropyltrimethoxysilane.

4. The dental material of claim 1, wherein the α-diketone, comprises camphorquinone.

5. The dental material of claim 1, wherein the α-diketone comprises a mixture of 0.01 to 1 weight % camphorquinone and 0.01 to 1 weight % of 9,10-phenanthrenequinone.

6. The dental material of claim 5, wherein (c) and (d) comprise a photoinitiator system comprising 0.02 to 0.05 weight % camphor quinone, 0.02 to 0.05 weight % 9,10-phenanthrenequinone, and 0.3 to 0.5 weight % dimethylaminobenzoic acid butoxyethyl ester.

7. The dental material of claim 6, which further comprises 0.2 to 0.5 weight % of an organic peroxide.

8. The dental material of claim 7, wherein the organic peroxide is selected from the group consisting of diacetylperoxide, dibenzoylperoxide and di-tert.-butylperoxide.

9. The dental material of claim 1, wherein the amine is selected from the group consisting of N,N-bis-(2-hydroxyethyl)-p-toluidine and esters of 4-dimethylaminobenzoic acid.

10. The dental material of claim 1, wherein the monomeric dimethacrylate component comprises bis-(4-(2-hydroxy-3-methacryloyloxypropoxy)phenyl)dimethylmethane and triethylene glycol dimethacrylate; the α-diketone comprises camphorquinone; the barium aluminum silicate glass is silanized with 3-methacryloyloxypropyltrimethoxysilane; and the silicon dioxide is silanized with 3-methacryloyloxypropyltrimethoxysilane.

11. The dental material of claim 10, wherein the amine is 4-dimethylaminobenzoic acid butoxyethyl ester.

12. The dental material of claim 10, wherein the amine is N,N-bis-(2-hydroxyethyl)-p-toludine.

13. The dental material of claim 12, wherein the α-diketone further comprises 9,10-phenanthrenequinone.

14. The dental material of claim 3, which further comprises 0.02 to 0.1 weight % of a benzoyl compound, and wherein the α-diketone comprises camphorquinone or a mixture of camphorquinone and 9,10-phenanthrenequinone.

15. The dental material of claim 14, further comprising 0.2 to 0.5 weight % of an organic peroxide.

16. The dental material of claim 15, in the form of a first paste and a second paste, wherein the first paste comprises
bis-(4-(2-hydroxy-3-methacrylolyloxypropoxy) phenyl) dimethylmethane and triethylene glycol dimethacrylate,
barium aluminum silicate glass with a mean particle size of 0.7 μm and silicon dioxide with a mean particle size of 0.04 to 0.06 μm, camphorquinone and 9,10-phenanthrenequinone, dimethylaminobenzoic acid butoxyethyl ester further comprises benzildimethylacetal, and
wherein the second paste comprises
triethylene glycol dimethacrylate and diurethane dimethacrylate made from 1 mol 2,2,4-trimethylhexamethylene diisocyanate and 2 mol 2-hydroxyethyl methacrylate,
barium aluminum silicate glass with a mean particle size of 0.7 μm and silicon dioxide with a mean particle size of 0.04 to 0.06 μm and further comprises
dibenzoylperoxide in an amount of 0.2 to 0.5 weight %.

17. The dental material of claim 1, consisting essentially of
(a) 14 weight % of bis-GMA and 7 weight % of triethylene glycol dimethacrylate;
(b) 69.7 weight % of barium aluminum silicate glass silanized with 3-methacryloyloxypropyltrimethoxysilane, and 8 weight % of silicon dioxide silanized with 3-methacryloyloxypropyltrimethoxysilane, said silicon dioxide having a mean particle size of 0.04 to 0.06 μm;
(c) 0.4 weight % of camphorquinone;
(d) 0.06 weight % of benzildimethylacetal; and
(e) 0.3 weight % of 4-dimethylaminobenzoic acid butoxyethyl ester.

18. The dental material of claim 1, wherein the amine is 4-dimethylaminobenzoic acid butoxyethyl ester.

19. The dental material of claim 18, wherein the inorganic filler mixture is silanized with 3-methacryloyloxypropyltrimethoxysilane.

* * * * *

UNITED STATES PATENT AND TRADEMARK OFFICE
CERTIFICATE OF CORRECTION

PATENT NO. : 5,228,907

DATED : July 20, 1993

INVENTOR(S) : EPPINGER et al

It is certified that error appears in the above-identified patent and that said Letters Patent is hereby corrected as shown below:

```
Column 7, line 5 (Claim 6):  delete "camphor quinone"
                and insert --camphorquinone--.
```

Signed and Sealed this

Thirteenth Day of June, 1995

BRUCE LEHMAN

*Attest:*

*Attesting Officer*           *Commissioner of Patents and Trademarks*